US006494886B1

United States Patent
Wilk et al.

(10) Patent No.: US 6,494,886 B1
(45) Date of Patent: Dec. 17, 2002

(54) OFF-SET CLAMP MECHANISM AND ASSOCIATED METHOD FOR MINIMALLY INVASIVE SURGERY

(75) Inventors: Peter J. Wilk, New York, NY (US); James R. Whitney, Morrisville, NC (US)

(73) Assignees: Granit Medical Innovation, Inc., New York, NY (US); Weck Closure Systems, LLC, Research Triangle Park, NC (US)

(*) Notice: Subject to any disclaimer, the term of this patent is extended or adjusted under 35 U.S.C. 154(b) by 291 days.

(21) Appl. No.: 09/602,103

(22) Filed: Jun. 22, 2000

(51) Int. Cl.$^7$ ................................................. A61B 17/10
(52) U.S. Cl. ...................................... 606/142; 606/205
(58) Field of Search .................................. 606/142, 157, 606/205, 206, 208, 210, 158; 128/898

(56) References Cited

U.S. PATENT DOCUMENTS

| | | |
|---|---|---|
| 943,263 A | 12/1909 | Moraweck et al. |
| 1,510,416 A | 9/1924 | Pietz et al. |
| 2,113,246 A | 4/1938 | Wappler |
| 2,384,697 A | 9/1945 | Riccardi |
| 2,968,041 A | 1/1961 | Skold |
| 3,378,010 A | 4/1968 | Codling et al. |
| 3,518,993 A | 7/1970 | Blake |
| 3,777,538 A | 12/1973 | Weatherly et al. |
| 3,882,854 A | 5/1975 | Hulka et al. |
| 3,958,576 A | 5/1976 | Komiya |

(List continued on next page.)

FOREIGN PATENT DOCUMENTS

DE  23 30 182  1/1975

OTHER PUBLICATIONS

Abstract—patent No. 5,749,879; May 12, 1998 in the name of Middleman et al.
Abstract—patent No. 5,904,690; May 18, 1999 in the name of Middleman et al.
Abstract—patent No. 5,820,628; Oct. 13, 1998 in the name of Middleman et al.
Abstract—patent No. 5,720,754; Feb. 24, 1998 in the name of Middleman et al.

(List continued on next page.)

Primary Examiner—David O. Reip
Assistant Examiner—Julian W. Woo
(74) Attorney, Agent, or Firm—R. Neil Sudol; Henry D. Coleman; William J. Sapone

(57) ABSTRACT

A surgical clamping device comprises a first jaw and a second jaw, with a self-locking surgical fastener mountable thereon. The jaws have at least a first closing configuration and a second closing configuration, the first closing configuration designed to reduce a lateral dimension of a clamping device with mounted fastener, without thereby engaging locking devices on the selflocking surgical fastener, the second closing configuration designed to cause an engagement of the self-locking devices, thereby allowing a demounting of the fastener and a permanent disposition thereof in tissue. In a first closing configuration an approximation of the jaws in a transverse plane thereof is accompanied by an out-of-plane movement, comprising translation, or rotation about an axis in the plane, the rotation in turn comprising twisting—rotation about an axis essentially parallel to a longitudinal axis of the jaws, or skewing—rotation about an axis essentially perpendicular to a longitudinal axis of the jaws. An alternative engagement of the first closing configuration and the second closing configuration is effected by a ratcheting device in conjunction with a camming device, or any means of actuation known in the mechanical arts.

15 Claims, 1 Drawing Sheet

U.S. PATENT DOCUMENTS

| | | |
|---|---|---|
| 4,038,987 A | 8/1977 | Komiya |
| 4,367,746 A | 1/1983 | Derechinsky |
| 4,394,864 A | 7/1983 | Sandhaus |
| 4,446,865 A | 5/1984 | Jewusiak |
| 4,485,817 A | 12/1984 | Swiggett |
| 4,496,090 A | 1/1985 | Crevier et al. |
| 4,512,345 A | 4/1985 | Green |
| 4,681,107 A | 7/1987 | Kees, Jr. |
| 4,706,668 A | 11/1987 | Backer |
| 4,714,075 A | 12/1987 | Krauter et al. |
| 4,735,194 A | 4/1988 | Stiegmann |
| 4,759,364 A | 7/1988 | Boebel |
| 4,796,627 A | 1/1989 | Tucker |
| 4,821,721 A | 4/1989 | Chin et al. |
| 4,841,888 A | 6/1989 | Mills et al. |
| 4,880,015 A | 11/1989 | Nierman |
| 4,887,612 A | 12/1989 | Esser et al. |
| 4,934,364 A | 6/1990 | Green |
| 4,945,920 A | 8/1990 | Clossick |
| 4,971,067 A | 11/1990 | Bolduc et al. |
| 4,983,176 A | 1/1991 | Cushman et al. |
| 5,015,249 A | 5/1991 | Nakao et al. |
| 5,049,153 A | 9/1991 | Nakao et al. |
| 5,156,609 A | 10/1992 | Nakao et al. |
| 5,222,961 A | 6/1993 | Nakao et al. |
| 5,304,204 A | 4/1994 | Bregen |
| 5,601,573 A | 2/1997 | Fogelberg et al. |

OTHER PUBLICATIONS

Abstract—patent No. 5,632,746; May 27, 1997 in the name of Middleman et al.

Abstract—patent No. 5,601,572; Feb. 11, 1997 in the name of Middleman et al.

Abstract—patent No. 5,833,700; Nov. 10, 1998 in the name of Fogelberg et al.

Abstract—patent No. 5,575,803; Nov. 19, 1996 in the name of Cooper et al.

Abstract—patent No. 5,549,628; Aug. 27, 1996 in the name of Cooper et al.

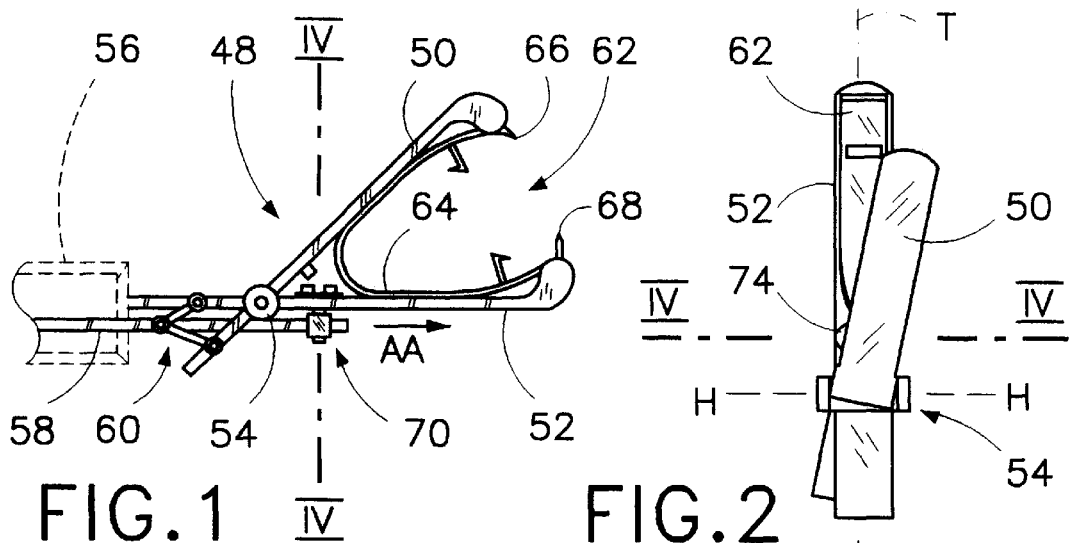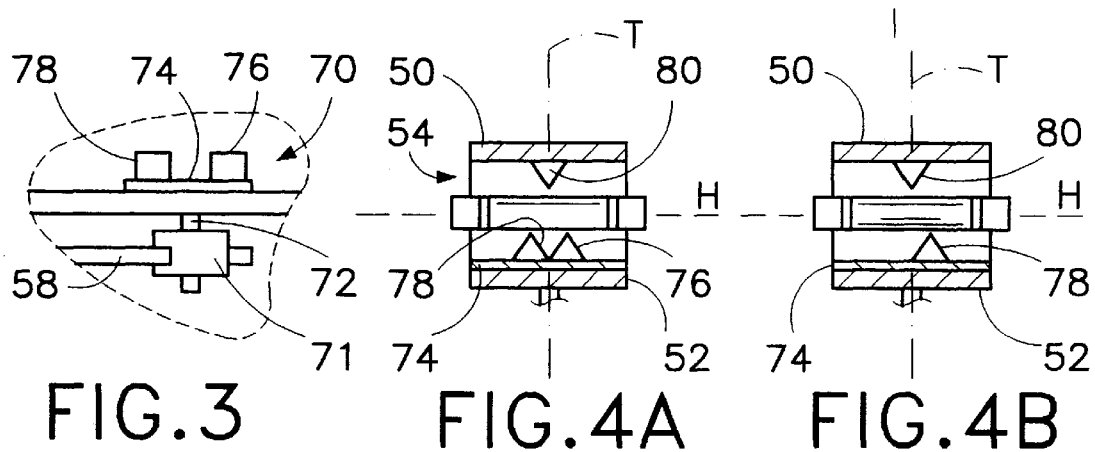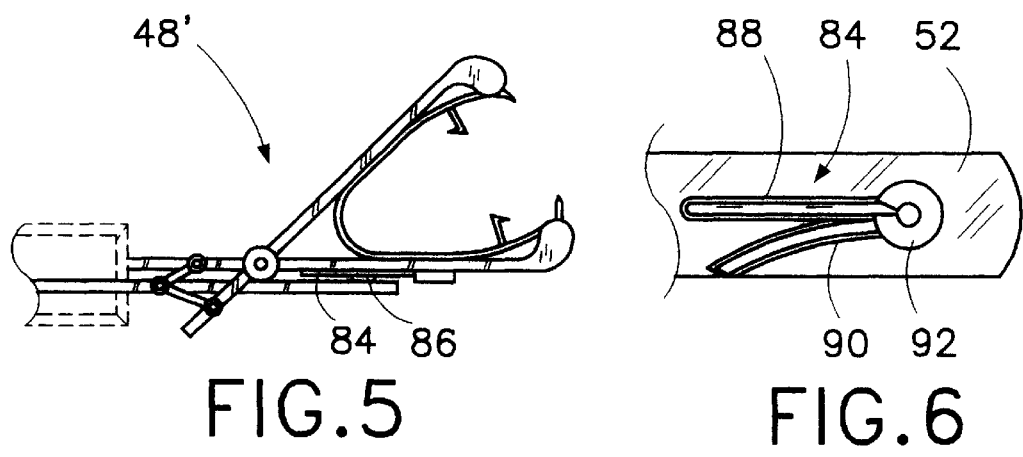

OFF-SET CLAMP MECHANISM AND ASSOCIATED METHOD FOR MINIMALLY INVASIVE SURGERY

FIELD OF THE INVENTION

This invention relates to the field of surgeries conducted through a tubular guide or cannula, including but not limited to arthroscopic, endoscopic, laparoscopic, thoracoscopic, and intravascular surgeries. In particular, this invention relates to instruments insertable through a cannula and carrying a surgical fastener to a distal end thereof. This invention also relates to a method for clamping organic tissues.

BACKGROUND

Various minimally invasive surgical techniques have been developed involving the passage of instruments down a tubular guide or cannula inserted into an existing orifice or duct of the human body, penetrating a bodily wall, or both. These techniques include, but are not limited to, arthroscopic, endoscopic, laparoscopic, thoracoscopic, and intravascular surgeries, although in laparoscopic surgery the tubular penetration may be limited to the bore of a trocar sleeve, an extended cannula being omitted. In these techniques, space, and in particular space perpendicular to a longitudinal or major extensive axis of a surgical instrument designed for insertion through a cannula, is at a premium. Devices which may be collapsed along one or two dimensions, opening to a full extension inside a patient and mechanisms allowing a compact insertion of an otherwise prohibitively large surgical device, will therefore find utility in minimally invasive techniques.

Positively or self-locking surgical clamps, such as those intended for occlusion of a sperm duct, occupy less space in a lateral dimension relative to a major axis of the clamp in a closed configuration than in an open configuration. However, by the very positive locking feature, i.e., by virtue of having a locking mechanism which permanently holds the clamp closed once the jaws are engaged, a clamp of this variety so closed cannot be conveniently opened. Holding such a clamp in a partially closed pre-firing configuration during an insertion is one method of reducing lateral space requirements. However, in order to achieve a maximum pre-firing compactness in a lateral dimension, a self-locking clamp would be ideally inserted in an essentially fully closed configuration, without thereby engaging the locking mechanism.

OBJECTS OF THE INVENTION

It is an object of the present invention to provide an instrument for use in minimally invasive surgical procedures.

It is a more particular object of this invention to provide a surgical clamping instrument adapted for insertion through a cannula, or other tightly confined opening.

Yet a more particular object of this invention is provide such a surgical clamping instrument for inserting a lockable surgical clamp in an essentially closed configuration pre-firing condition, without thereby engaging the locking mechanism.

An associated object of the present invention is to provide a method for clamping organic tissues in a surgical procedure.

An additional related object of the present invention is to provide such a method for particular use in minimally invasive procedures wherein surgical operations are effectuated through a narrow tubular guide or cannula.

These and other objects of the invention will become apparent through an inspection of the description and figures hereunder.

SUMMARY OF THE INVENTION

A insertion device for a surgical clamp or fastener in accordance with the present invention includes a set of jaws having at least one opened configuration and two closed configurations, the closed configurations comprising an in-line configuration and a skewed or off-set configuration. In the offset configuration, the jaws hold the fastener in a distorted essentially closed state so that locking elements on legs of the fastener do not engage one another, enabling the fastener to be opened upon insertion of the jaws and the fastener into a patient. In the in-line configuration of the jaws, the jaws close the fastener about intervening organic tissues of the patient, enabling engagement of the locking elements and a locked closure of the fastener.

Pursuant to another feature of the present invention, the jaws are placed in the offset configuration by a skew motion of at least one of the jaws, which may be defined as a rotation of the jaws about a secondary axis perpendicular to a rotation axis of a jaw hinge and also perpendicular to a longitudinal axis of the jaws: rotation about the longitudinal axis would alternatively constitute a relative torquing or twisting motion of the jaws.

Pursuant to one step of a method in accordance with the present invention, the jaws are disposed in an open configuration, pre-mounted with a self-locking clamp or fastener, and then closed into the in-line configuration, resulting in an engagement of locking elements on the fastener, and a permanent closure of the fastener. Subsequently opening the jaws disengages the jaws from the now set fastener and allows withdrawal of the device from an operating site. In contrast, closing the jaws in the offset configuration prevents an engagement of the locking elements, while still substantially closing the fastener. An ability to close the jaws without engaging the locking elements of a positively locking fastener allows the fastener to be first inserted through a narrow cannula or other limited aperture with substantial space savings. The jaws in general will have to be returned to a substantially closed position after disengaging or dismounting of the set fastener, to allow removal of the device through the same cannula.

It is apparent that it must be possible to close the jaws in a first or second closed configuration in a useful order. In a simplest method, an alternation of skew and in-line motions is realized on alternate closures. This alternating motion is achieved by one of two mechanisms or medical instruments pursuant to the present invention.

In a first mechanism or instrument, the instrument device has a lower jaw, rigidly mounted to a sheath or stalk defining a major longitudinal axis of the instrument. An accompanying upper jaw is attached to the lower jaw at a hinge or pivot point. The sheath serves as a guide for a drive rod or post, which is, at a distal tip of the instrument, is essentially constrained to move in parallel to the lower jaw. A linkage engaging the drive rod is connected to lower and upper jaws, and urges the jaws apart, in an opened configuration, when the rod is forced outward, in a distal direction, with respect to the sheath. Conversely, when the rod is withdrawn in an opposite the jaws are urged together into a closed configuration. A distal tip of the drive rod further engages a ratcheting mechanism mounted under the lower jaw, which in turn drives a control wheel mounted in an angle of the jaws, on the lower jaw, via a shaft. The ratcheting mechanism rotates the control wheel a fixed amount, 180° in the present embodiment, upon each distal extension of the rod.

The control wheel is provided on an upper surface with two camming devices, which alternatively engage a wedge or tooth mounted on an under surface of the upper jaw. In a locking position of the wheel, a V-shaped guide receives the tooth and aligns the jaws to force an engagement of self-locking elements on a mounted surgical fastener upon closing of the jaws. In a skewing position of the wheel, a second wedge deflects the wedge or tooth on the upper jaw, causing a skewing motion of the jaws and preventing an engagement of the locking elements on the fastener. In this configuration, the jaws may be essentially closed, achieving a minimum lateral dimension, without positively locking an attached surgical fastener. In order to allow a desired range of motion of the jaws, a hinge having a pre-determined amount of mechanical "slop" or tolerance is employed, the V-shaped guide serving to effect a positive in-line closure in a first position of the wheel. Alternatively, a partial ball or universal joint may be employed.

In a second mechanism or instrument in accordance with the present invention, a substantially similar design of sheath, drive rod, hinge and jaws are utilized. However, the wheel and camming devices are eliminated. In their place a guide track is mounted on a lower surface of the lower jaw, engaging a substantially vertical pin projecting from a distal end of the drive rod. The track is comprised of two branches, which come together at a distal end thereof, meeting in a ratcheting or switching device. Upon each distal extension of the drive rod, the ratcheting device is engaged at an extreme of the motion, and alternatively redirects the rod into a first branch and a second branch of the track.

Upon engagement of the pin or projection in a first, straight, branch of the track, the jaws are drawn together in-line upon a withdrawal of the drive rod, effectuating engagement of locking elements of an attached surgical fastener. Alternatively, upon engagement of the pin in a second, curved, branch of the track, the drive rod is forced out of alignment with respect to the lower jaw and longitudinal axis of the instrument, and the upper jaw, is compelled by a bending of the rod, via the linkage engaging the rod and the jaws, out of alignment with the lower jaw, and thereby closes in an offset configuration.

An additional degree of mechanical tolerance is included in the linkage in the second embodiment relative to the first embodiment, to allow a bending motion of the rod to be translated to a skew motion of the jaws. Alternatively, partial universal joints are employed in the linkage.

An instrument in accordance with the present invention enables the application of a surgical clip or fastener to internal tissues of a patient via a natural or surgically formed opening in the patient which is substantially smaller than the opened configuration of the clip or fastener.

BRIEF DESCRIPTION OF THE DRAWINGS

FIG. 1 is a schematic side elevational view of functional elements of a clip application instrument in accordance with the present invention, showing instrument jaws and the clip in an opened configuration.

FIG. 2 is a schematic top elevational view of the instrument of FIG. 1, showing a skewed or offset relationship of the jaws.

FIG. 3 is a side elevational view, on a larger scale, of a ratchet mechanism shown in FIG. 1 for enabling closure of the jaws alternately in an aligned configuration and the offset configuration of FIG. 2

FIGS. 4A and 4B are schematic partial end elevational views of the mechanism of FIG. 3, showing different stages in the use of the instrument of FIGS. 1 and 2.

FIG. 5 is a schematic side elevational view of functional elements of another clip application instrument in accordance with the present invention, showing instrument jaws and the clip in an opened configuration.

FIG. 6 is a schematic elevational view of a guide part of the clip application instrument of FIG. 5.

DETAILED DESCRIPTION OF THE EMBODIMENTS

A first embodiment of an instrument for setting a self-locking surgical clamp or fastener, as shown in FIG. 1, includes a clamping mechanism 48 at a distal end thereof (not designated), comprising an upper jaw 50 and a lower jaw 52 joined at a hinge or pivot point 54. The lower jaw is joined to a rigid elongate sheath 56 which in turn substantially houses a drive rod 58. Drive rod 58 actuates an opening and closing motion of the jaws from a proximal end (not shown) of the instrument. A linkage 60 joins the drive rod to jaws 50, 52 on a proximal side of hinge 54, and is designed to urge the jaws into a open configuration when rod 58 is pushed in a distal direction AA, or alternatively draw the jaws into a closed configuration when the rod is withdrawn in a proximal direction opposite to direction AA, as indicated in FIG. 1.

Hinge 54 is designed with mechanical tolerances in order to permit a full range of rotation of the jaws about a hinge or primary axis H (FIG. 2), and a limited degree of secondary rotation about a secondary axis (not shown) perpendicular to the primary axis. The secondary axis may either be essentially parallel to plane IV—IV (FIG. 1) or else perpendicular to plane IV—IV and essentially parallel to a transverse plane T (FIG. 2), or a combination of these two orientations. Where the secondary axis is essentially parallel to plane IV—IV, the secondary rotation is a skewing rotation, as seen in FIG. 2, rotating the upper jaw 50 out of transverse plane T. Where the secondary axis is essentially perpendicular to plane IV—IV, the secondary rotation is a torquing or twisting rotation (not shown), about an axis contained in T—T and the plane of FIG. 2.

A self-locking surgical spring-clip or fastener 62 is shown mounted on jaws 50, 52, preparatory to a surgical fastening operation. Clip 62 is biased to assume a normally open position, as illustrated in FIG. 1, by internal spring forces in a main clip member or body 64. The spring-clip includes a pair of locking elements 66, 68 designed to interfere and subsequently engage in a locking sequence upon a closing of the clip. Following the locking sequence, the clip remains in a closed configuration in a mechanically strained state, supplying compressive forces to internal organic tissue (not shown) which may be trapped by jaw tips 66, 68. When mounted in the open position on the jaws of the clamping device, a surgical fastener is said to be in a pre-firing configuration.

A remainder of the instrument (not shown) comprises an extension of sheath 56 and rod 58, terminating in a handle and trigger mechanism, for manipulation of the instrument in toto and control of the drive rod. In a surgical clamping operation, a proximal handle section of the instrument remains external to a patient, while a distal portion of the instrument including the clamping mechanism and a substantial portion of the sheath, are inserted into the patient through a cannula or narrow tubular access into an internal somatic cavity.

In order to effectuate an alternate skewing and in-line closing action of the jaws, a camming mechanism 70 is mounted on lower jaw 52, a more detailed view of the mechanism being shown in FIG. 3. Camming mechanism includes a ratcheting device 71 mounted on a shaft 72 which penetrates lower jaw 52; ratcheting device 71 in turn receives a distal end (not separately designated) of drive rod 58. Adjacent to an upper surface of jaw 52, a camming wheel 74 is mounted to an upper end (not designated) of shaft 72. Wheel 74 is provided with a pair of diametrically opposed cogs or camming surfaces 76, 78 designed to operatively engage a tooth 80 provided on a bottom side of upper jaw 50. Camming surface 76 is formed with a V-shaped groove 82 for receiving tooth 80 in transverse plane T of lower jaw 52 during a closing motion of the jaws, while camming surface 78 is wedge-shaped and is designed to deflect tooth 80 out of plane T.

Ratcheting device 71 advances shaft 72 one-half revolution for every complete cycle of rod 58, i.e., every cycle of a distal jaw opening movement followed by a proximal jaw closing movement of the rod. Accordingly, each alternating closing movement of the jaws finds wheel 74 in an alternate position, presenting first surface 76 and subsequently surface 78 for interaction with tooth 80. Accordingly, every second closing movement of jaws 50, 52 actuated by the handle and trigger mechanism (not shown) via drive rod 58 results in a skewing of the jaws (FIG. 2), which in turn prevents an engagement of locking elements 66, 68. A remainder of closures of the jaws occur inline and result in an engagement of locking elements in a mounted surgical clip.

A second embodiment of an instrument for setting a self-locking surgical clamp or fastener is shown in FIGS. 5 and 6. Clamping mechanism 48' is structurally similar to mechanism 48, with an elimination of ratcheting device 71, shaft 72, camming wheel 74 and tooth 80. Instead, a camming effect is achieved by a camming track 84, which engages a vertical pin or projection 86 mounted on drive rod 58. Camming track 84 is in turn comprised of a straight branch 88 and a curved branch 90, which branches meet in a ratcheting device 92. Ratcheting device 92 redirects pin 86 alternatively down the straight branch 88 and down the curved branch 90 upon each distally extreme movement of the pin, in a filly opened configuration of the jaws. Upon an engagement of curved branch 90, a resulting deflection of drive rod 58 is communicated to a proximal end 94 of the upper jaw through a modified linkage 60'. Linkage 60' enjoys an enhanced degree of mechanical tolerance relative to linkage 60, allowing an additional freedom of movement to generate a skewing motion of jaws 50, 52. In all remaining particulars, a mode of operation of the first embodiment and the second embodiment of an instrument for setting a self-locking surgical clamp are essentially identical.

The instruments are first placed in an open configuration anticipating a skew-closure, while external to a patient. A self-locking surgical clip or fastener is mounted in jaws 50, 52, and a first, skew, closure of the jaws is effected via the handle and trigger mechanism. Following the first closure, the instrument is inserted through a cannula into a patient, and the jaws allowed to open once the distally located clamping mechanism is located in an intended bodily void. Following an opening of the jaws, the instrument is set to positively lock the surgical fastener on a next closing, which closing is effectuated as desired to seize and compress tissue. Following a setting or positive closure of the fastener, the jaws are first allowed to open, to release the fastener, and then re-closed in a skew configuration for withdrawal through the cannula. After an additional half-cycle effected with the jaws in an empty condition, to place the instrument again in a pre-skew condition, a second fastener is loaded, and the cycle is repeated.

DESCRIPTION OF ADDITIONAL EMBODIMENTS

Other geometric embodiments of the invention may be contemplated (none illustrated). In general, a pair of jaws having normal directions perpendicular to major surfaces thereof may be so disposed that the normal direction of a first jaw and the normal direction of a second jaw lie in a common plane, called a transverse plane. The configuration so described generalizes the configuration of FIG. 1, wherein a normal direction or vector of the lower jaw and a normal vector of the upper jaw both lie in a plane T, being a basal plane of the drawing. In general a first mode of approximation or closing of the jaws prevents engagement of locking devices of a self-closing surgical fastener mounted thereon, while a second mode permits such engagement. The second mode preserves the normal vectors of the jaws in a common plane is a mode which may compress a clip or fastener with upper and lower prongs having similar normal vectors without twisting or skewing, thereby leading to an engagement of adjacent locking elements. Such a second mode of approximation may consist of a pure rotation of the jaws about an axis—equivalent to a hinge axis—perpendicular to the common plane, or else a translation in the common plane without rotation, such as a closure of the jaws maintaining a parallel orientation. A combination of these movements is also possible. A first mode of approximation combines the second mode with an additional movement of the jaws out of the common plane. Such an additional movement may comprise a rotation of one or both jaws about an axis lying in the common plane, or else a translation out of the plane. Given appropriate geometric magnitudes, such an additional movement combined with the second mode of approximation will suffice to prevent an engagement of locking elements on a selfclosing fastener mounted on the jaws, which elements would otherwise be engaged by an approximation of the jaws.

Other embodiments (not illustrated) may vary the motive power and control mechanisms of the jaws of the clamping mechanism. In the detailed description, camming mechanisms are disclosed for control mechanisms, and a manually actuated drive rod for mechanical motive power. For the purposes of this specification, a camming mechanism is defined as a mechanical control device having a first surface and a second surface, the second surface being constrained to ride on or follow contours of the first surface. A wedge deflected by a wedge or a pin constrained to ride on a track meet the definition of a camming device. Other modalities combining control and motive power which would readily occur to one skilled in the construction of mechanical manipulators include electrical servo-motors, electromagnets, hydraulic actuators, and standard mechanical gearing combined with an available source of rotatory or linear power. It is also possible to preload a disposable, single-use, clamping devices embodying the principles of the present invention. Yet another optional embodiment combines a clamping device and a self-closing medical fastener in a single unit, which is detached and left inside a patient in toto following a clamping operation, similar to a traditional use of live ants as suturing devices, by a removal of the ant body from ant head and mandibles following a piercing and closure of wound edges by the mandibles or jaw parts.

Accordingly a scope of the invention is to be understood primarily in terms of the claims, and in the geometric principles involved, rather than in terms of a particular mechanical embodiment as described herein.

What is claimed:

1. A method for clamping tissue, comprising:

providing a self-locking surgical fastener and a clamping device for applying said fastener to organic tissues, said clamping device a pair of jaws, said fastener being located between said jaws in an offset closed configuration of said jaws;

passing said jaws and said fastener through a cannula into a patient;

thereafter moving at least one of said jaws so that said jaws assume an open configuration;

shifting the opened jaws so that said jaws and portions of said fastener are disposed on opposite sides of a selected portion of internal organic tissues of the patient; and after the shifting of the opened jaws, moving at least said one of said jaws so that said jaws assume an aligned closed configuration, whereby said fastener is applied to the selected portion of the internal organic tissues of the patient.

2. The method of claim 1 wherein said jaws are provided with a hinge having a hinge axis, and the moving of said one of said jaws includes a rotation about said hinge axis.

3. The method of claim 2 wherein said jaws have an essentially common longitudinal axis in said aligned closed configuration, the moving of said one of said jaws further including a secondary rotation about an axis essentially perpendicular to said longitudinal axis.

4. The method of claim 1 wherein the providing of said fastener and said clamping device includes inserting said fastener between said jaws in an open prefixing configuration of said jaws and moving at least said one of said jaws so that said jaws assume said offset closed configuration.

5. The method of claim 1 wherein said clamping device has a longitudinal axis and a transverse plane oriented at an angle to said axis, the moving of said one of said jaws including shifting at least said one of said jaws by a primary movement in said transverse plane and a secondary movement out of said transverse plane.

6. A method for clamping tissue, comprising:

providing a self-locking surgical fastener;

providing a clamping device for setting said fastener, having a first jaw, a second jaw and a transverse plane, said jaws being initially in an open configuration mounted with said fastener;

shifting said jaws into a first closed configuration by a primary movement in said transverse plane, and a secondary movement out of said transverse plane;

passing said jaws and said fastener through a cannula into an internal cavity of a patient;

following said passing, returning said jaws to an open configuration; and shifting said jaws into a second closed configuration by a movement in said transverse plane, in order to clamp an intervening moiety of tissue and activate a locking feature of said self-locking surgical fastener.

7. The method of claim 6 wherein said jaws are provided with a hinge having a hinge axis, and said primary movement comprises a rotation about said hinge axis.

8. The method of claim 7 wherein said jaws have an essentially common longitudinal axis in a closed configuration, and said secondary movement out of comprises a secondary rotation about an axis essentially perpendicular to said longitudinal axis.

9. The method of claim 6 including a step of demounting said fastener, by at least a partial opening of said jaws, following said shifting into a second closed configuration.

10. The method of claim 9 including a step of restoring said jaws to a closed position following said demounting, and removing said clamping device from said patient.

11. The method of claim 6 including a step of mounting said fastener on said clamping device.

12. A surgical fastening device, comprising:

a first jaw;

a second jaw;

a hinge, operatively connected to said first jaw and said second jaw, having a primary axis;

a drive mechanism, for closing said jaws; and a camming mechanism, operatively connected to said drive mechanism, for alternatively closing said jaws with a first net rotation and a second net rotation, said first net rotation comprising a major component about said primary axis and a minor component about a secondary axis perpendicular to said primary axis, said second net rotation being essentially about said primary axis.

13. The fastening device of claim 12 wherein said camming mechanism comprises a first wedge operatively connected to said first jaw and a second wedge operatively connected to said second jaw, said second wedge being disposed to engage said first wedge for closing said jaws with said first net rotation.

14. The fastening device of claim 12 wherein said camming mechanism comprises a mechanical projection, operatively connected to a component of said drive mechanism, and a track, operatively connected to said second jaw, whereby said projection engages said track for alternatively guiding a closing of said jaws in said first net rotation and said second net rotation.

15. A surgical fastening device, comprising:

a shaft;

a first jaw coupled to a distal end of said shaft;

a second jaw movably coupled to said distal end of said shaft;

a drive operatively connected to at least said second jaw for closing said jaws; and a displacement mechanism, operatively connected to said second jaw, for shifting said second jaw out of alignment with said first jaw in alternate closures of said second jaw, so that said jaws are alternately closed in an aligned configuration and an offset configuration.

\* \* \* \* \*